United States Patent [19]

Gaiser et al.

[11] 4,346,840

[45] Aug. 31, 1982

[54] VOLATILE DISPENSING COMPOSITION AND METHOD

[76] Inventors: Laurel A. Gaiser, 2528 Fifth Ave., Sacramento, Calif. 95818; Conrad J. Gaiser, P.O. Box 534, Zephyr Cove, Nev. 89448

[21] Appl. No.: 67,340

[22] Filed: Aug. 17, 1979

Related U.S. Application Data

[63] Continuation-in-part of Ser. No. 742,560, Nov. 17, 1976, abandoned.

[51] Int. Cl.$^3$ ................................................ A61L 9/04
[52] U.S. Cl. ......................................... 239/6; 239/54; 239/55
[58] Field of Search .............................. 239/34, 53–60, 239/6; 424/76; 252/522 A

[56] References Cited

U.S. PATENT DOCUMENTS 2,988,284  6/1961  Smith ..................................... 239/54
3,630,446  12/1971  Roth et al. ........................ 239/60 X

OTHER PUBLICATIONS

Balsam et al., Cosmetics Science and Technology, vol. 1, 2nd Ed., pp. 339 and 348.

Primary Examiner—Andres Kashnikow
Attorney, Agent, or Firm—Fischer, Tachner & Strauss

[57] ABSTRACT

There is disclosed a deodorant composition which has its volatile components such as perfume and deodorant components each adsorbed onto an inert solid carrier. Preferably a plurality of volatile components of different relative volatilities are each adsorbed onto an inert solid carrier to provide a plurality of component-bearing, solid fractions which are blended together in preselected portions to provide the desired proportional release rate of each of the volatile components. The blended solid fractions are packaged into a volatile releasing container. The composition does not exhibit the shrinkage characteristic of other compositions such as solid deodorants and can be provided with a controlled and constant relative release rate of its volatile component throughout its useful life.

12 Claims, 12 Drawing Figures

VOLATILE DISPENSING COMPOSITION AND METHOD

REFERENCE TO RELATED APPLICATION

This is a continuation-in-part of application Ser. No. 742,560, filed on Nov. 17, 1976 now abandoned.

BACKGROUND OF THE INVENTION

1. Field of the Invention

This invention relates to a composition of a volatile component having a preselected and constant volatile release rate throughout its life and, in particular, to a deodorant composition of a plurality of volatile components and a method for their preparation.

2. Brief Statement of the Prior Art

Compositions such as room deodorants and the like comprise a volatile perfume agent in a liquid solution or a gel cake. The product evaporates and the concentration of the volatile agent and size of the solid cake steadily decreases, resulting in deodorants that exhibit steadily decreasing release rate of the volatile perfume agent. Deodorants also are frequently formed with a plurality of volatile ingredients, e.g., the perfumes and odor masking agents may be a blend of several perfumes, agents and various solvents, or other ingredients of different volatilities employed in the composition. This also causes changes in the amount and composition of the released vapor.

The deodorant compositions are employed in a variety of vapor-releasing forms. Some of the deodorants are consolidated into a cake or solid composite, frequently using a deliquescent or sublimating material such as napthalene, paradichlorobenzene, soap, and the like. The solid cake is placed in a container having a closure member which can be removed or positioned to release the active agents. Liquid deodorant compositions are employed with wicks and the like to provide a surface for releasing the volatile ingredients, the user controlling the release rate by the extent of exposure of the wick of the package.

The aforedescribed deodorant compositions have a number of disadvantages. The solid deodorants unavoidably shrink during their life and have a steadily decreasing release rate proportional to their steadily decreasing surface area. The liquids exhibit a similar declining release rate resulting from a decreasing concentration of the volatile agent in the liquid. Often the deodorant compositions have a plurality of volatile components, and these compositions unavoidably change during use such that the proportions of the ingredients which are released from the deodorant constantly change. Additionally, the manufacture of the packages of deodorant, either liquid or solid form, are needlessly complicated by the physical state of the composition. The usual inert carrier, a soap or gel, is costly to prepare and handle and contributes substantially to the manufacturing cost of the final product.

BRIEF STATEMENT OF THE INVENTION

This invention comprises a volatile agent dispensing product which is adsorbed onto a solid carrier to control the release rate of the volatile agent. Preferably, a product of the invention includes a plurality of volatile components which are each adsorbed onto an inert solid carrier having a preselected surface area in relation to its volume and adsorption isotherm characteristics to obtain a plurality of component-bearing solid fractions. The solid fractions are blended together at preselected concentrations to provide the desired proportional release rate of each of the volatile components. The resultant blend is then packaged into a volatile releasing form, e.g., in a container with a removable sealing member which can have provision for controlling the total release rate from the package. The invention achieves a number of beneficial results. One can provide a series of products, in containers of identical dimensions and net contents but with different release rates, by variation in the particle size of spherical or substantially spherical carrier particles. On can also select the carrier and its proportions for each volatile component of a product which best maintains the desired vapor composition.

BRIEF DESCRIPTION OF THE DRAWINGS

The invention will be described with reference to the drawings of which.

DESCRIPTION OF THE PREFERRED EMBODIMENTS

Figures 1, 2, 3:
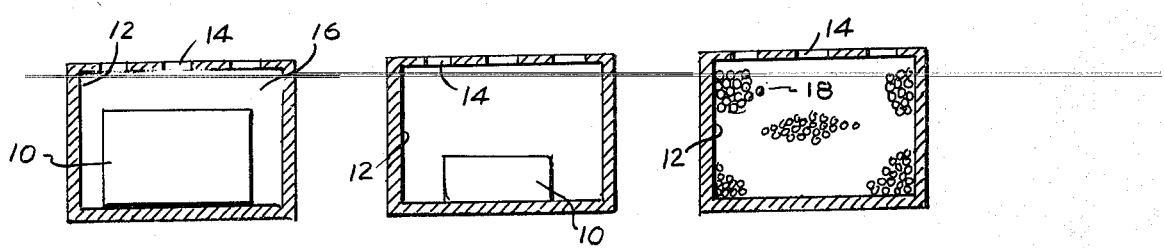
FIGS. 1 and 2 illustrate the change in volume or a prior art solid deodorant during its life.
FIG. 3 illustrates the lifetime condition of a deodorant according to the invention.

The invention comprises a deodorant product of a volatile perfume or masking agent adsorbed onto an inert solid particulate carrier. The solid extends the useful life of the deodorant and provides a substantially constant evaporation surface for the perfume agent throughout the life of the product.

In its preferred embodiment, the deodorant product comprises a composition of a plurality of volatile ingredients of distinctly different vapor pressures. The method of manufacture of this composition includes the adsorption of each of the volatile indredients onto an inert solid adsorbent with preselection of one or more of the following: specific surface area, particle size, adsorption isotherm characteristic, or loading (concentration of absorbate on the solid) to obtain a plurality of component-bearing, solid fractions. The solid fractions are blended together in preselected proportions to provide a proportional release rate of each of the volatile adsorbates which produces the desired vapor composition; and the resultant blend is packaged into a volatile releasing form, such as in a container with a removable seal or closure member. In the preferred method one selects different sizes of a solid carrier which are loaded to saturation or near saturation with respective volatile agents and the resultant solid fractions are blended together in the proper proportions to obtain the desired release rate of each volatile agent.

In a preferred embodiment, the volatile product, of one or a plurality of volatile components, is provided as a series of packaged products of the same overall container size and shape and net weight but with distinctly different rates of release of the volatile agent. This permits the product to be packaged and marketed as a series of different volatilities in identical containers. The difference in volatilities are imparted by selection of spherical or subsubstantially spherical (spheroidal) inert particles of different size ranges to provide varied evaporation surface area to each of the product series without any substantial change in the bulk or net weights of the product.

The deodorant composition may include a perfume agent which can be a blend of a plurality of odorous materials. The ingredients of the composition are each adsorbed onto a solid, particulate adsorbent to provide a preselected and controlled proportional release rate of each of the substances during the life of the deodorant composition to maintain throughout such life a constant relationship among the ingredients in the vapor phase.

The perfumes which can be employed can be of flower oils such as obtained by distillation or solvent extraction of cultivated flowers; essential oils usually obtained by steam distillation of plant materials such as leaves, fruits, roots, etc.; animal substances such as extracts of civit, ambergris, musk, etc.; or resinoids, balsams, etc. Synthetic odorous materials can also be employed.

The flower oil which can be used will generally be employed in small proportions to give the deodorant a pleasing odor and temper the harshness of materials such as essential oils, resinoids and the like. The most common flower oils are rose and jasmine, however, other flower oils such as violet, bitter orange tree, mimosa, tuberose, etc. can also be employed.

The essential oils, which are obtained usually by steam distillation of plant materials and which can be used in the invention include lavender, sandalwood, rosewood, citronella, geranium, vetivert, oak moss, bergamot, orris, citrous oils, etc.

Concentrates of the essential oils usually obtained by distillation or extraction are available under the designation of isolates. Of these, materials such as citronellol, geraniol, citral, can be used. Various synthetic materials having similar odorous characteristics to these materials are also available.

The animal origin materials are usually employed in relatively minor quantities to empart a lasting quality to the deodorant, often exhibiting a synergistic affect on the odor of the perfumes. Examples of these are extracts of musk, civet, ambergris, castoreum, etc.

The resinoids which can be employed include myrrh, styrax, benzoin, olibanum, galbanum, etc.

Typically the deodorant employs a relatively low concentration of the perfume substance; from one to about twenty weight percent, usually from two to about ten percent. The balance of the deodorant composition comprises a solvent or liquid carrier such as alcohol, e.g., isopropanol, ethanol, butanol, isobutanol, etc. Other solvents which can be employed alone or in combination with any of the foregoing substances include the glycols such as propylene glycol, ethylene glycol, etc.

Any of a wide variety of finely subdivided solids can be used as the solid adsorbent for the volatile ingredients. Typical of these materials are titania, zirconia, alumina, silica, etc., or combination of these materials. Examples include silica, Fuller's earth, diatomaceous earth, calcium or sodium silicates, expanded calcium silicate (pearlite), expanded sodium silicate, alumina, silica stabilized alumina containing from 1 to 15 percent silica as described in U.S. Pat. No. 2,437,532, the aluminum silicates, clay, naturally occurring or synthetically prepared zeolites such as chabazite, gnelenite or faujasite, as well as synthetic zeolites. The latter materials are partially dehydrated crystalline compositions of silica and alumina and contain quantities of 1 or more exchangeable cations such as sodium, potassium, hydrogen, magnesium, calcium, etc. The compositions and their preparation are described in U.S. Pat. Nos. 2,882,243 and 2,882,244. These compositions are characterized by crystal pores of relatively uniform pore diameter between about 5 and 14 Angstrom units. Several crystal forms of such molecular sieves are available and suitable for use herein as the carrier for the volatile perfume agents of my invention including the X, Y, L and J crystal types. Other materials which can be used include botanical flours such as soybean flour, wheat flour, tobacco flour, cottonseed flour walnut shell flour, wood flour, sawdust, etc. Other materials that can be used include particulate solid metal carbonates and sulphates. Examples of suitable carbonates include calcite and dolomite. A suitable sulfate is gypsum.

The size range of the particles can be widely varied to provide the desired control over the volatile release rate. Typically, solids having a particle diameter of one inch and less and retained on about a number 120, U.S. Standard size sieve can be used, corresponding in particle diameters from 1.0 inch to about 0.005 inch. Preferably, the size range of solids is from number 3 to about number 16 size sieve, corresponding to particle diameters from about 0.25 to 0.05 inch. The use of more finely subdivided particles is not desirable since such particles significantly reduce ventilation and air circulation through the product, resulting in an undesirably low rate of release of volatile agent.

When the size range of the solid adsorbent is used to control the release rate of a volatile component or agent, the solid particles are preferably of a medium to narrow size range, e.g., solid fractions passing and retained on screens differing by about 1 to 5 numbers, preferably 1 to about 3 numbers, on the aforementioned U.S. Standard screen size scale.

Referring now to FIGS. 1, there is illustrated a typical solid, cake deodorant 10, characteristic of the prior art. The volatile perfume agent is incorporated in a soap or gel composition which is placed within a container or package 12. The container is provided with a seal or closure member (not shown) which is removed or punched to provide a plurality of apertures 14 permitting escape of the volatile perfume agent. While the solid cake initially fills the chamber 16 within container 12 after its employment, the deodorant reaches a condition such as illustrated in FIG. 2 where the solid cake 10 is only a fraction of its original volume and occupies only a portion of chamber 16 within container 12. The surface area which is available for release of the volatile agent is the surface area of the solid cake 10, and it can be seen that this surface area is only a fraction of the original surface area shown in FIG. 1.

The deodorant product according to the invention is illustrated in FIG. 3 as typical of the physical state of the product throughout its useful life. The product can also be packaged in a container 12 having a plurality of apertures in a wall or cover thereof for escape of the volatile constituent. The deodorant according to the invention, however, is adsorbed onto a particulate inert solid 18 which is placed within container 12, substantially filling the container with the particulate solids. The total surface of the solids, which is the product of the specific surface area times the net weight of the solids within the container 12, is the surface for release of the volatile constituent. This surface area will remain constant throughout the life of the deodorant product since the solid is a nonvolatile material and does not diminish in volume during the life of the product. Consequently, the deodorant product of the invention can be characterized by a substantially constant volatile release rate throughout its life and is relatively free of the declining release rate characteristic of the prior art.

Figure 4:
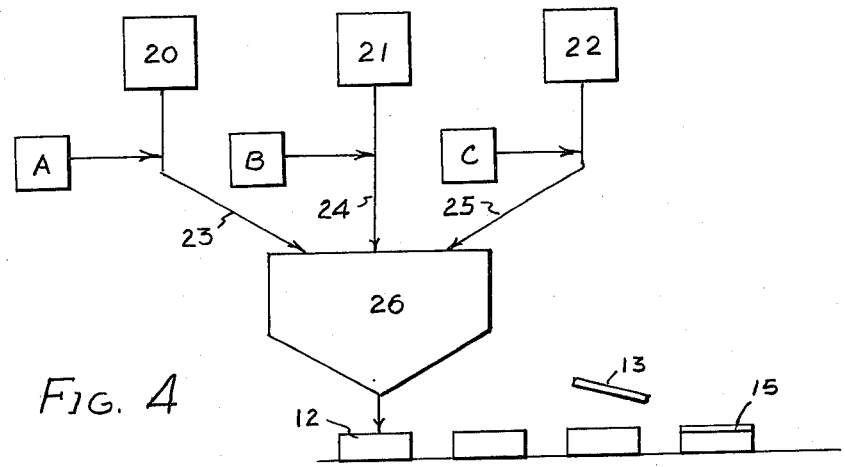
FIG. 4 illustrates the method of manufacture of a preferred deodorant composition.

FIG. 4 illustrates a method of manufacturing a deodorant product according to the invention wherein the product comprises a mixture of a plurality of volatile constituents A, B, C, . . . . In the practice of this embodiment of the invention, each of the volatile constituents A, B, and C are adsorbed onto a solid 20, 21, or 22 having a preselected specific surface area and particle size, thereby providing a plurality of volatile component bearing solid fractions which are passed through lines 23, 24 and 25 into admixture in hopper 26 where the solid fractions are blended together in preselected proportions. The relative proportions of the solids blended into the final mixture in hopper 26 as well as the identity, particle size and specific surface area of the solids employed are correlated with the volatility and adsorptivity of their respective volatile fractions to provide a product comprising a blend of adsorbate bearing solid fractions that will provide a release of vapor of the proper and constant proportions of components A, B, and C initially and throughout the life of the composition. After blending of the components in hopper 26, the components can be dispensed into containers 12 which are provided with suitable seals or closures 13 to obtain a finished, packaged product 15 suitable for marketing.

The characteristic of volatile materials adsorbed on an inert solid adsorbent can be conveniently depicted by an adsorption isotherm which is a plot of the absorbate vapor pressure against its volume adsorbed on a constant amount of adsorbent. For inert solid adsorption, the mechanism is physical adsorption which consists of monolayers, multilayers and/or condensation of the adsorbate as a liquid in the capillaries of the adsorbent. Physical adsorption phenomenon is generally accepted to result from physical or Van der Walls forces between the adsorbate and the solid adsorbent.

Figures 5, 6, 7:
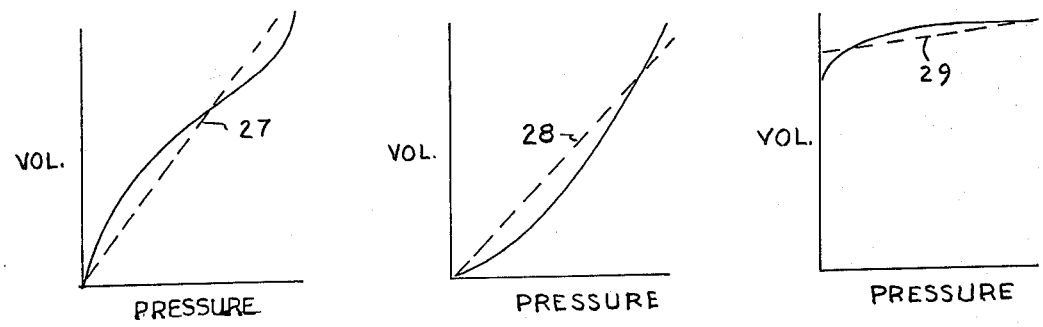
FIGS. 5-7 illustrate typical adsorption isotherms.

FIGS. 5-7 illustrate typical adsorption isotherms. The isotherm illustrated in FIG. 5 is characteristic of adsorption of a vapor as thick multilayers of the adsorbate on the surface of the adsorbent. FIG. 6 illustrates a typical isotherm which is characteristic of the adsorption of a gas or vapor on a solid in which the heat of adsorption is less than the heat of liquification of the vapor. FIG. 7 illustrates another adsorption phenomenon representative of the adsorption of a vapor on a solid adsorbent in monomolecular film thicknesses.

FIGS. 5-7 thus illustrate that the vapor pressure of an adsorbate decreases along a predictable and known relationship as the concentration of the adsorbate on the solid adsorbent decreasees. This relationship can be approximated by an average, straight-line relationship as shown by the broken lines 27, 28 and 29 for each of FIGS. 5, 6 and 7. To provide a substantially constant release rate of a volatile deodorant through its life, a combination of solid adsorbent and volatile agents having an adsorption isotherm comparable to that of FIG. 7 can be selected.

Figure 8:
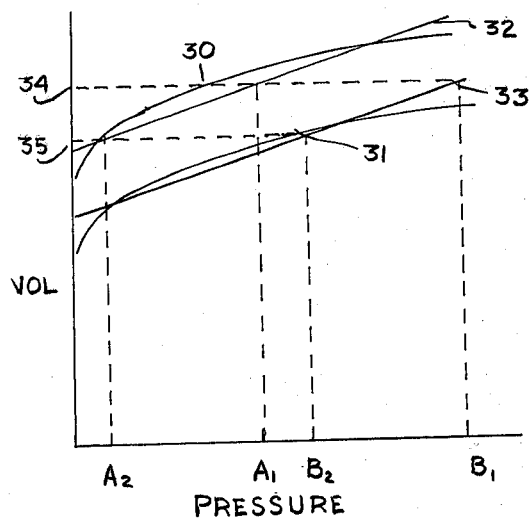
FIG. 8 illustrates the adsorption isotherms of a deodorant blend of a plurality of volatile fractions according to the invention.

The invention is practiced by providing the combination of solid adsorbent and vapor, or volatile perfume agent, that will provide approximately matching adsorption isotherm characteristics. This is illustrated in FIG. 8 in which the adsorption isotherm of a physical blend of volatile component A bearing solid fraction and volatile component B bearing solid fraction are blended together. The adsorption isotherm of the solid fraction bearing volatile component A is shown by the curved line 30 while that of the solid fraction bearing volatile component B is illustrated by the curved line 31. These volatile components A and B are adsorbed onto adsorbents which provide the adsorbtion isotherms of the same general configuration, typically that shown in FIG. 7. This type of adsorption is generally exhibited by non-polar volatile components which are adsorbed on a solid adsorbent such as characoal. Accordingly, most of the volatile perfume agents previously described, which are non-polar compounds, can be convenient adsorbed on a material such as charcoal to provide solid fractions of adsorption isotherms of approximately the same configuration.

The average behavior of the adsorbate of these fractions is depicted by the straight lines 32 and 33 for components A and B, respectively. Since the straight line average characteristic of the adsorbates are substantially parallel, it can be seen that the vapor pressures of the volatile components are in substantially constant proportion, resulting in the release of a vapor of substantially constant concentration of components A and B throughout the life of the composition. This is illustrated by the two points 34 and 35 on the volume concentration scale; line 34 corresponding to the initial or early condition of the deodorant composition when the material has a high proportion of volatile components and point 35 corresponding to a more aged or used composition having a lower total concentration of volatile components.

Figure 9:
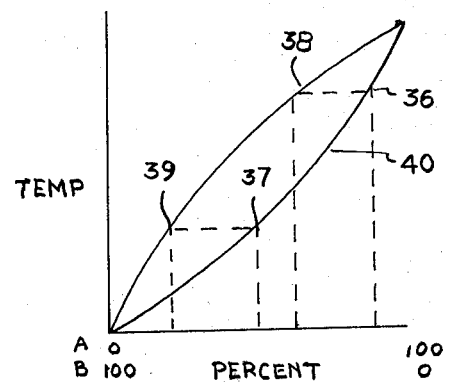
FIG. 9 illustrates the changing vapor composition characteristic of liquid deodorants.

The aforedescribed behavior of the composition according to the invention contrasts sharply with the typical liquid mixture of deodorant materials. The liquid mixture has a volatile release characteristic such as that illustrated in FIG. 9 which is a graphical depiction of the vaporization curve of a liquid mixture of components A and B. If the liquid mixture initially is at a composition indicated by point 36, approximately 90 percent of volatile component A and 10 percent of component B, the vapor composition in equilibrium with this liquid is that shown by point 38 in which the concentration of component A is only about 58 percent. As this deodorant is used, the liquid fraction becomes increasingly concentrated in component A following the arrowheaded line 40. At the composition of point 37, approximately 50 percent volatile component A and 50 percent volatile component B, the material will release a vapor composition of that shown by point 39 which is approximately 15 percent of component A and 85 percent of the less volatile component B. Accordingly, a typical liquid mixture of two volatile components will produce a vapor composition which continuously changes during the useful life of the deodorant composition.

Figures 10, 11, 12:
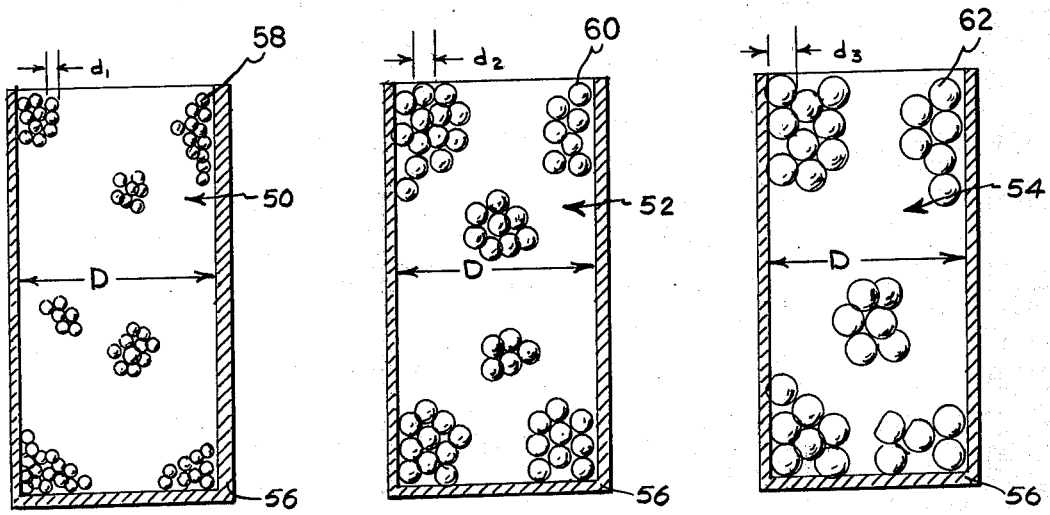
FIGS. 10-12 illustrate another embodiment of the invention.

Referring now to FIGS. 10-12, there is illustrated a series of deodorant products 50, 52 and 54 which are packaged in containers 56 of identical shape, generally cylindrical, and of identical capacity. Each of the containers is filled with a solid fraction, 58, 60, and 62, respectively, which bear an adsorbate of a volatile perfume agent. The average particle diameter of each of these solid fractions is illustrated as $d_1$, $d_2$, and $d_3$ in progressively increasing diameters. The overall diameter of the container is shown as D. With the provision that the solid particles are spherical or general spherical in configuration, so long as the solids' diameter is less than about 20 percent of the container diameter d, the total weight of solids within the containers for products 50, 52 and 54 are substantially equal. Accordingly, the content weight of each of the products can be maintained substantially equal while providing a filled or substantially filled container for each of the products.

The evaporation surface for release of the volatile agent, however, varies directly with the average particle diameter of the solids. The evaporation surface for each of the products is proportional to the ratios of their respective surfaces to volumes which are as follows:

$$\text{Volume} = 4/3\pi r^3$$

$$\text{Surface} = 4\pi r^2$$

$$\text{Surface/Volume} = 3/r$$

Since, within the aforementioned limits of spherical particles of the range of particle diameters, the total volumes are equal, the total surface areas, therefore vary inversely with the average diameter of the particle solid fraction.

It is, therefore, apparent that the invention enables one to provide a series a deodorant products packaged in identical and filled containers with a preselected and varied rate of release of the volatile perfume agent between the products simply by the expedient of variation in the average particle diameter of the solid fraction of the adsorbent which carries the volatile adsorbate. In the illustrated embodiment, if the relative proportion between the average diameters are such that $d_2$ is 1.5, and $d_3$ is 2.0 times the diameter of $d_1$, the product 52 will have 1.5 times greater, and product 50 will have 2 times greater, volatility than that of product 54.

The invention has been described with illustration of the presently preferred embodiments thereof. It is not intended that the invention be unduly limited by the illustrated and preferred embodiments. Instead, it is intended that the invention be defined by the means and steps, and their obvious equivalents, set forth in the following claims.

What is claimed is:

1. A method of providing a plurality of volatile-dispensing products of the same volatile-dispensing composition and bulk volume but with varied volatility which comprises adsorbing the volatile-dispensing composition onto a plurality of varied size range fractions of an inert solid adsorbent carrier of spherical or substantially spherical particles and packaging each of the resultant adsorbate-solid fractions of varied particle size range into containers having a cross-sectional diagonal at least about 5 times the average particle diameter of said adsorbent particles.

2. The method of claim 1 wherein said solid adsorbent is silica.

3. The method of claim 1 wherein said solid adsorbent is expanded calcium silicate.

4. A product to release a deodorant vapor mixture of a plurality of volatile deodorant ingredients comprising a package of a mixture of a plurality of volatile-deodorant-bearing fractions, each fraction comprising an adsorbate of one of said volatile deodorant components adsorbed onto inert solid carrier particles having particle diameters from 0.005 to 1 inch, and each fraction having a preselected, proportional release rate of its respective volatile component by preselection of one or more of solid particle specific surface area, adsorbate concentration, particle size and adsorption isotherm characteristics and being present at a concentration to provide a mixture of deodorant vapor released from said product that is of a preselected, desired composition throughout its useful life.

5. The product of claim 4 wherein said solid fractions have preselected absorption isotherm characteristics to release a vapor mixture of substantial constant composition throughout the useful life of said product.

6. The product of claim 4 wherein said solid carrier is charcoal.

7. The product of claim 4 wherein said solid carrier is silica.

8. The product of claim 4 wherein said solid carrier is expanded calcium silicate.

9. The product of claim 4 wherein said volatile-dispensing composition is a deodorant.

10. In a packaged product series wherein all packages comprise a preselected, single size cylindrical vessel and contain a volatile component intended for dispensing into the atmosphere with preselected and distinct rates varying between said packages, the improvement which comprises:
(a) a volatile ingredient for dispensing into the atmosphere; and
(b) an inert solid adsorbent of spherical or substantial spherical particles having diameters less than 20 percent of the diameter of said vessel and having adsorbed thereon said volatile ingredient, with the particles having a preselected size variation between said packages to provide a series of a packaged volatile component in equal exterior size packages and weights with preselected varied volatile release rates.

11. The product of claim 10 wherein said solid adsorbent is silica.

12. The product of claim 10 wherein said solid adsorbent is expanded calcium silicate.

* * * * *